United States Patent
Cramer

(10) Patent No.: US 10,424,398 B2
(45) Date of Patent: Sep. 24, 2019

(54) METHOD FOR ALIGNING MOLECULES IN THREE DIMENSIONS BASED UPON THEIR CORRESPONDENCE TO AN EXEMPLARY TEMPLATE MOLECULE FOR USE IN PERFORMING 3D QSAR ANALYSES

(71) Applicant: Richard D. Cramer, Santa Fe, NM (US)

(72) Inventor: Richard D. Cramer, Santa Fe, NM (US)

( * ) Notice: Subject to any disclaimer, the term of this patent is extended or adjusted under 35 U.S.C. 154(b) by 149 days.

(21) Appl. No.: 14/337,832

(22) Filed: Jul. 22, 2014

(65) Prior Publication Data

US 2015/0025871 A1    Jan. 22, 2015

Related U.S. Application Data

(60) Provisional application No. 61/857,216, filed on Jul. 22, 2013, provisional application No. 61/857,668, filed on Jul. 23, 2013.

(51) Int. Cl.
*G16C 20/50*   (2019.01)

(52) U.S. Cl.
CPC .................................. *G16C 20/50* (2019.02)

(58) Field of Classification Search
None
See application file for complete search history.

(56) References Cited

U.S. PATENT DOCUMENTS

| | | | |
|---|---|---|---|
| 6,735,530 B1 * | 5/2004 | Guarnieri | 702/27 |
| 8,504,302 B2 * | 8/2013 | Cramer | 702/19 |
| 2011/0018866 A1 * | 1/2011 | Downes et al. | 345/419 |

\* cited by examiner

*Primary Examiner* — Michael L Borin
(74) *Attorney, Agent, or Firm* — Day Pitney LLP

(57) ABSTRACT

A computerized procedure for aligning molecules for use in CoMFA or other 3D QSAR methodologies does not rely on fragmentation of the molecules instead, aligning molecules based upon comparison to identified template molecules. Initially an anchor bond is identified in the candidate and template molecule that have similar atoms at each end of the bonds. The anchor bond need not be an acyclic bond. The candidate molecule is overlaid onto the template molecule by aligning the anchor bonds. Starting and working away from the anchor bond, matching atoms or atom types between the candidate and template molecule are identified. Once all matching atoms have been identified, the 3D coordinates of the template atoms are assigned to the corresponding atoms in the candidate molecule to place the candidate molecule into alignment.

4 Claims, 1 Drawing Sheet

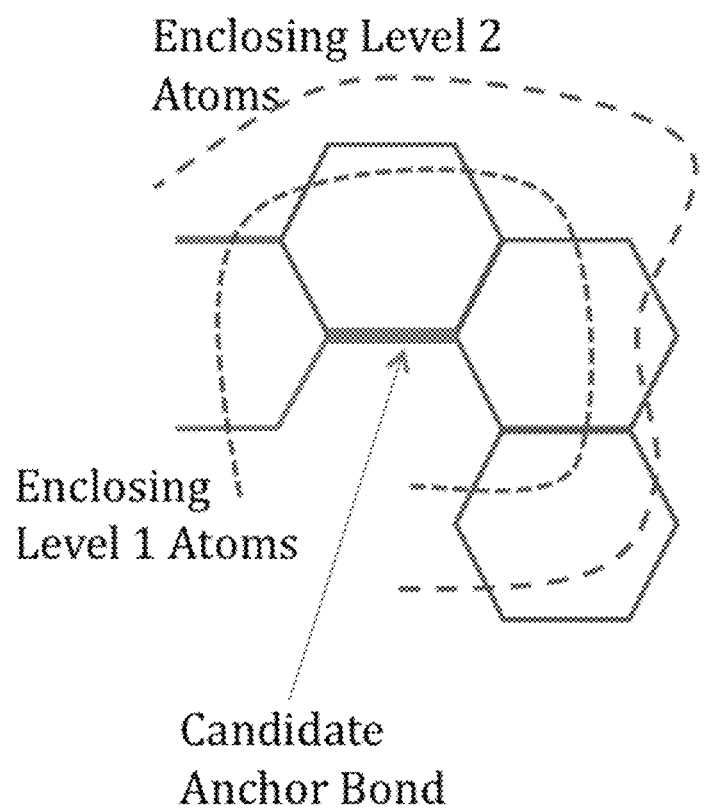

METHOD FOR ALIGNING MOLECULES IN THREE DIMENSIONS BASED UPON THEIR CORRESPONDENCE TO AN EXEMPLARY TEMPLATE MOLECULE FOR USE IN PERFORMING 3D QSAR ANALYSES

CROSS REFERENCE TO RELATED APPLICATION(S)

Benefit of U.S. Provisional Patent Application No. 61/857,216 filed on Jul. 22, 2013 and U.S. Provisional Patent Application No. 61/857,688 filed on Jul. 23, 2013 is hereby claimed.

BACKGROUND OF THE INVENTION

Field of the Invention

This invention relates generally to a computer implemented drug discovery method. More specifically, the disclosed method permits a user to specify a three dimensional representation of a template molecule, which may be derived from binding data, crystallographic data, modeling data, or any other source, to align additional molecules to generate a CoMFA (comparative molecular field analysis) QSAR.

Description of Related Art

In U.S. Pat. No. 5,025,388 and U.S. Pat. No. 5,307,287 Comparative Molecular Field Analysis (CoMFA), a three-dimensional quantitative structure activity relationship (3D QSAR) technique was introduced. The CoMFA technique permits a quantitative correlation of the observed activities of several molecules active in the same biological assay to the shape characteristics of those molecules. In CoMFA, each molecule in the activity series is aligned in a three dimensional grid and its shape characterized by the steric and electrostatic interactions energies between a probe and the atoms of the molecule at each grid point. The interaction energies are associated with the observed/measured activity of the molecule in a CoMFA table and a partial least squares (PLS) statistical analysis with validation is performed.

The resulting analysis provides coefficients of each grid location term in the table that reflects that position's contribution to the observed activity. Using the data, it is possible to identify and observe those volumes of the molecule (arrangement of atoms) associated with either increased or decreased activity. Based on the identified coefficients, it is also possible to estimate the likely biological activity of a molecule for which no activity has yet been determined in an assay.

However, CoMFA requires great care in the selection of molecular conformations and the proper alignment of the series of molecules, but, nevertheless, the technique demonstrated the power of utilizing three dimensional shape descriptors in molecular analysis, and CoMFA has become a fundamental method in computational chemistry.

Since the introduction of CoMFA many different procedures have been utilized to align the molecules of the activity series in the three dimensional grid. Proper alignment among all the molecules in the activity series is extremely important since any misalignment results in differences in the steric and electrostatic interaction energy shape descriptors that would not be related to the actual shape characteristics responsible for activity. Ideally, the molecules in the activity series could be aligned to an x-ray crystallographic structure determined for one of the molecules. However, for many active molecules, such a structure is not available. Alternatively, the series could be aligned to a conformation derived from a proposed binding site structure. The difficulties with whole molecule alignments have led to the development of alternative methods of examining and relating differences in molecular structure to activity.

Alternate 3D representations of molecular fragments, such as topomerically aligned fragments, have been developed and have been successfully employed. These approaches utilize fragmentation of the molecules in an activity series at acyclic bonds, topomerically aligning the fragments, characterizing the shape of the fragments utilizing the steric and electrostatic interaction energies as used in CoMFA, and comparison to the shape of fragments (similarly aligned and characterized by steric and electrostatic interaction energies) derived from libraries of molecular compounds. In particular, the 3D QSAR technique known as Topomeric CoMFA has been highly successful when used in conjunction with molecular fragments derived from a combinatorial library. It has been discovered that the Topomeric CoMFA approach could be extended to searching and deriving predicted activities from molecular fragments generated from large library assemblages of molecules that can be commercially obtained that do not derive from combinatorial syntheses and come from many different sources and syntheses, some known, some unknown. These libraries may, and do typically, contain natural products. Fragmenting at all the acyclic bonds in these molecules produces a much greater shape variation as well as number of molecular fragments than found by fragmenting the molecules of a combinatorial library. This approach has been taught in U.S. patent application Ser. No. 12/045,511 using a fragmentation on-the-fly technique first taught in U.S. Pat. No. 7,330,793.

However, as noted in U.S. Pat. No. 7,329,222 the use of a rule based (topomeric) procedure for aligning molecular fragments that lies at the heart of the Topomeric CoMFA methodology is not always applicable and may result in 3D fragment conformations that do not approximate those assumed by the fragment in an active molecule. Importantly, there are many cases where it is believed that an alternative geometric alignment, based on knowledge about receptor site geometry gleaned from other sources, such as x-ray studies or ligand binding, might be more useful in computing a 3D QSAR such as CoMFA. Alternatively, it may be desirable to seek alignments that overlay fragments from two or more structurally non-congeneric sets that may, for example, be known to bind to the same receptor. To handle these situations, an alternative alignment method was devised which could align such structurally varied fragments to some user specified geometry or geometries. This alignment method supplants the topomeric alignment method used with fragments in U.S. Pat. No. 7,330,793, and U.S. patent application Ser. No. 12/045,511. However, construction and use of the CoMFA data table proceeds as taught in those patents.

U.S. Pat. No. 8,504,302 teaches a new alignment method which permits alignments of molecular fragments to one or more user supplied templates that specify the types and three dimensional positions of all the atoms in one or more molecular fragments. Fragmentation of the query molecules that comprise the activity set as well as molecules examined in the database libraries is performed as taught in the cited patent documents. The fragment template to which alignment is made need not come from any fragment derived from a molecule in a congeneric series but only from a template molecule selected by the user. However, any fragment from a congeneric series could be used as a template fragment as well. In U.S. Pat. No. 8,504,302, reference to the template or template atoms means the externally specified 3D arrangement of atoms and their types. Reference to the candidate or candidate atoms means the arrangement of atoms and their types found in the fragments derived from the molecules in a congeneric series. In the method atom-by-atom matches (identical atoms) between the template fragment and the candidate fragment are identified by serial/sequential traversals that start at the fragment root and end wherever no more matches exist along any given branch. To align the candidate fragment, for atoms in the candidate fragment (excepting partial matches within rings) that match atoms in the template fragment, the coordinates of the matching template atoms are assigned to the candidate atoms. Once the common alignment is established, a useful CoMFA analysis may be performed.

DESCRIPTION OF THE FIGURE

FIG. 1 indicates schematically the identification of an anchor bond and the atoms that are included in different atom layers.

DETAILED DESCRIPTION OF THE INVENTION

Computational Chemistry Environment:

Software code to practice the present invention may written by one skilled in the art based upon the written description provided herein. In addition, software code provided as part of the disclosure of the United States Patents listed below may be readily employed.

Generally, all calculations and analyses to perform the method of the present invention are implemented utilizing a specifically programmed computer employed in a modern computational chemistry environment using software designed to handle molecular structures and associated properties and operations. For purposes of the present application, such an environment is specifically referenced. In particular, the computational environment and capabilities of the SYBYL and UNITY software programs developed and marketed by Tripos, Inc. (St. Louis, Mo.) are specifically utilized. Software with similar functionalities to SYBYL and UNITY are available from other sources, both commercial and non-commercial, well known to those in the art.

A general-purpose programmable digital computer with a fast CPU, ample amounts of memory, hard disk storage, display screens and printer outputs is required for the implementation of this invention. In performing the methods of this invention, representations of thousands of molecules, molecular structures, and fragments as well as other data may need to be stored simultaneously in the random access memory of the computer or in rapidly available permanent storage. The inventor uses any of a variety of currently available desktop or laptop computers meeting the above requirements and running Linux, Windows, or Macintosh operating systems to practice this invention. Since a user of the method of the invention disclosed in this patent document can best understand and study the output and the computational shape analysis visually, especially given the enormous number and diversity of chemical structures analyzed, a display screen and system capable of visualizing and manipulating images of the three dimensional shapes is used. Chemists are generally some of the most visually oriented scientists when thinking about chemical structures and, therefore, a visualized output on a computer screen of the computational analysis matches their visual approach. Alternatively, selected results can be either captured as screen images or printed out on hard copy.

Referenced Patents

The entire disclosure of the methods taught in the following patent documents U.S. Pat. No. 5,025,388, U.S. Pat. No. 5,307,287, U.S. Pat. No. 6,185,506, U.S. Pat. No. 6,240,374, U.S. Pat. No. 7,136,758, U.S. Pat. No. 7,184,893, U.S. Pat. No. 7,329,222, U.S. Pat. No. 7,330,793, U.S. patent application Ser. No. 12/045,511, and U.S. Pat. No. 8,504,302 including the software code which forms a part of the patent disclosures are incorporated herein as if fully set forth.

Template Alignment of Molecules:

While the generation of a 3D QSAR utilizing CoMFA with topomerically aligned fragments has produced significant results, the question remains of whether some useful information is lost when molecules are fragmented at acyclic bonds and placed into a uniform, but "unnatural" 3D topomeric pose. In addition, there is no way to utilize the additional 3D information that the structure of a receptor bound ligand provides. Fragmentation approaches have nothing to do with receptors or receptor based design.

The present invention provides several fundamental advances over the method disclosed in U.S. Pat. No. 8,504,302 that enable new and previously impossible approaches to aligning molecules for CoMFA or other 3D QSAR analysis. As disclosed in the patents cited above, correct alignment of molecules to be used in a 3D QSAR is a critical step. This is so because any characterization resulting from misalignment will be interpreted by the 3D QSAR as a difference between the molecules, when, if fact, such difference is not, in actuality, a characteristic of the molecules. The method taught in U.S. Pat. No. 8,504,302 represented the best state-of-the-art approach to molecular alignment previously possible. However, as noted above, it relied on fragmenting both the template and candidate molecules at acyclic bonds. Considering the abundance and importance of cyclic structures in medicinally important molecules, the restriction to fragmentation at acyclic bonds potentially ignored important 3D structural realities.

The first major advance over the prior art is that, unlike the fragmentation methods taught in earlier patents, the present method does not fragment molecules at any bond, acyclic or not. The purpose of the present alignment procedure is to align the entirety of each candidate molecule to the most similar of one or more template molecules. Note that this procedure is in stark contrast to that used in topomeric alignments of fragments where a rule based alignment was applied to all fragments in order to create a consistent alignment.

In place of the fragmentation bond previously taught in U.S. Pat. No. 8,504,302, the present invention teaches the identification and use of an "anchor bond", which, most importantly, is not limited to an acyclic connection. As taught below, the template and candidate molecules are compared atom-by-atom starting at the anchor bond. When there are multiple templates molecules, the templates must be superimposed in the same manner as they are known to, or thought to be, aligned at their receptor target.

A second major advance results from the fact that, since the "anchor bond" approach does not require fragmentation or artificial alignments, it is now possible to extend the utility of 3D QSAR techniques, such as the CoMFA method, beyond that taught in the prior art by making possible the simultaneous use of several congeneric series. This feature of the present invention allows the integration of 3D structural data from multiple congeneric series into one QSAR analysis. Molecules from multiple congeneric series can be aligned to one or more common template molecules. Further, not only does the present invention solve the long standing problem of uniformly aligning whole (non-fragmented) molecules for a CoMFA/3D QSAR analysis, but it also permits the direct integration and use of 3D data derived from other types of physiochemical analysis (x-ray, receptor based studies, etc.) to generate the 3D QSAR. In fact, should a molecule be known that does not belong to a structural series but which has an appropriate matching activity, that molecule can be similarly aligned and included in the CoMFA analysis.

A third major advance of the "anchor bond" method of the present invention, is that all realistically possible alignments between candidate molecules and one or more template molecules can be explored by automating the selection of the anchor bond to sequentially use every bond in the molecules. This automated procedure can be applied to large numbers of congeneric molecules to produce the best alignments for use in a comprehensive CoMFA analysis.

Application Examples:

The following examples illustrate the application and power of the inventive method:

Example 1 a congeneric series that possess similar activities with the same receptor aligned to a template molecule (where the template is a 3D structure template believed representative of the series).

Significantly, the method also for the first time solves the problem of aligning molecules in the following cases:

Example 2 a congeneric series aligned to multiple templates;

Example 3 multiple congeneric series that possess similar activities with the same receptor aligned with one template;

Example 4 multiple congeneric series that possess similar activities with the same receptor aligned with multiple templates;

Example 5 non-congeneric molecules that that possess similar activities with the same receptor aligned with one template;

Example 6 non-congeneric molecules that possess similar activities with the same receptor aligned with multiple templates.

It should be appreciated that the inventive method relies upon knowledge of the 3D coordinates (from x-ray, pharmacophoric, receptor site modeling data, or other means) for one or more template molecules to which the candidate molecules will be aligned. Example 1 consists of a series of structurally similar molecules whose 3D coordinates are unknown. Example 2 takes a congeneric series and aligns it to multiple templates where two or more template structures are known or proposed.

Example 3 is characterized by multiple series of congeneric molecules which series do not share the same structural similarity but which have activity at the same receptor and are aligned to one template. Example 4 aligns multiple congeneric series which do not share the same structural similarity but which have activity at the same receptor to more than one template. Example 5 aligns to one template, molecules that do not share structural similarity but which have activity at the same receptor. Finally, Example 6 aligns to multiple templates molecules that do not share structural similarity but which have activity at the same receptor.

To accomplish these alignments, the application of the method to the simplest first case of Example 1 will be described. The extension to the other 5 examples will then be discussed. Initially, an "anchor bond" is selected that has an identifiable counterpart in all the congeneric (candidate) molecules as well as in the template molecule. This anchor bond may be the bond between any two atoms found in the candidate and template structures and may or may not be a bond occurring in a ring structure. For this first discussion, the anchor bond is chosen by the user of the method. As will be discussed later, the selection of the anchor bond can be automated. For the present discussion, it is sufficient to note that in Example 1, once an anchor bond in the template molecule is identified, the automated procedure can sequentially match all anchor bonds in the candidate molecule in a sequential application of the method to determine which candidate anchor bond yields the best alignment.

Once the candidate anchor bond is selected, the 3D structures of the candidate molecules in the series are generated (such as by programs like Concord or Corina). The alignment procedure then proceeds. The anchor bond of a first candidate molecule is superimposed onto the anchor bond of the template molecule and all the matching atoms in the two molecules are identified. The 3D coordinates of the matching atoms are copied from the template molecule onto the atoms of the candidate molecule. For cases where no matching atoms exist, the remaining coordinates for the atoms in the candidate molecule are generated using the standard topomer protocol. Each of the candidate molecules is sequentially taken up and the 3D coordinates assigned to each. These coordinates are then used to place each candidate molecule in the three dimensional CoMFA grid for QSAR analysis. The following is a summary of the procedure including the variations required.

The six stages of the overall alignment procedure may be summarized as follows:

Stage 1: The user identifies in both the molecules in the congeneric series and the candidate template molecule an anchor bond.

Stage 2: 3D structures are generated for candidate molecules using a 3D structure generating program such as Concord or Corina. Candidate molecules are oriented by superimposing the candidate attachment bond onto the template attachment bond.

Stage 3: For both template and candidate molecules, all atoms (and atom property/types) are identified excluding all hydrogen atoms.

Stage 4: Atom-by-atom matches (identical atoms) between the template and the candidate are identified by serial/sequential traversals that start at the anchor bond and ends wherever no more matches exist along any given branch.

Stage 5: To align the candidate molecule, for atoms in the candidate molecule (excepting partial matches within rings) that match atoms in the template, the coordinates of the matching template atoms are assigned to the candidate atoms. Position any atoms in the candidate molecule that do not have matching atoms in the template so as to maintain their relative positions to those atoms in the candidate molecule that had matching atoms in the template. For each alignment, apply one of the sequences described below depending on whether there was any degree of match or no match at all.

Stage 6: For any branch that includes uncoordinated-copied atoms where the root of any branch will be a bond between a coordinate-copied and a coordinate-uncopied bond use the topomer alignment rules or any similar systematic procedure to consistently place the atoms in the branch.

Stage 7: If there is more than one template, each template is prepared as described in stages 1-3, and stage 4 is repeated for each template. A single final alignment for the candidate molecule is automatically chosen from these results, typically as the template that provides the largest number of atom-to-atom matches in stage 4.

In order to perform a template based alignment, it is necessary (stage 3) to first identify all the atoms (and atom types) found in the candidate molecule that are identical to those found in the template molecule. A complete matching (both atom type and atom properties are identical) is highly unlikely so that a partial match-identification method is also employed. After the atoms (and types) are identified, the candidate molecule is aligned.

Stage 4 Procedure—Atom Matching:

In stage 4, the identification of those atoms in the candidate molecule that match atoms in the template molecule is performed in two successive modes. Analysis in both modes proceeds from atom layer to atom layer. FIG. 1 indicates schematically the identification of an anchor bond and the atoms that are included in different atom layers. The first mode requires an exact match between candidate and template atom types and properties in each atom layer, and continues atom layer by atom layer until the next exact match criterion fails in a subsequent atom layer. The second mode, invoked when the first mode fails, requires only an approximate match between candidate and template atom types and properties. As the comparison goes forward, a list of those atoms that match at each layer is generated.

Exact Mode Stage 4:
a) The process starts by matching the atoms defining the candidate molecule anchor bond to the atoms defining the template anchor bond and proceeds by a breadth-first ("layered") processing of the remaining atoms in the candidate molecule. The list is updated to reflect each exact match.
b) For each non-hydrogen atom in the current layer of the candidate molecule for which an exact match has been identified, identify all its attached non-hydrogen atoms within the candidate molecule in the next atom layer.
c) Similarly, for the (previously identified) matching atom in the template, identify all its attached non-hydrogen atoms in the next atom layer.
d) Since there may be more than one way to exactly match each of the candidate attached atoms onto the individual template attached atoms, including the possibility of more or fewer atoms at the next atom layer in either the template or candidate, each of the atoms in the next candidate atom layer must be matched against each of the atoms in the next template atom layer until all permutations of candidate atoms to template atoms at that layer have been checked.
e) Every exactly matching permutation that is encountered in step d) is retained for further processing and extension, steps b) and c) then being applied to each permutation independently. Processing of an individual permutation ends whenever none of the atoms identified in step b exactly matches any of the atoms identified in step c.
f) The overall process stops when there are no more exact matches between any of the attached atoms in the candidate and to any of the attached atoms in the template, for any active permutation.

In "exact" mode, to accept a match between a candidate atom and a template atom, their atomic elements, and the type and ring status of their bonds to the previous atom layer must agree.

Approximate Mode Stage 4:

The approximate mode comparison process is implemented as follows. In the approximate mode, any acyclic heavy atom in the candidate matches any heavy atom in the template. And, in order to ensure that the resulting candidate molecule can initially be positioned regardless of how well its atoms match those in the template, any candidate heavy atom will match any template heavy atom, regardless of any disagreement in atom or bond properties, until the processing of the fourth heavy atom layer begins.

A match to any cyclic heavy atom beyond the third layer of the candidate does require similarity in atom types and bond properties, in contrast to the exact mode that requires agreement. However, the requirement for any of these three classes of agreement can be modified by the user.

To prevent excessive proliferation of acceptable permutations, whenever a permutation generates multiple permutation offspring, only a single "most promising" permutation is retained. "Most promising" is defined as the permutation having the smallest sum of differences in the numbers of the still unmatched atoms within candidate and template, compared attached atom by attached atom.

When transitioning from "exact" to "approximate" mode, the set of potentially active permutations remaining from the "exact" mode is re-examined in the approximate mode.

The approximate mode and therefore step 4 terminates whenever any of the following conditions occurs:
a) all heavy atoms in the candidate have been matched to template heavy atoms
b) no heavy atoms in the template remain unmatched by candidate atoms
c) none of the permutations can be extended without violating an active atom or bond match criterion. At the completion of the approximate mode, the identification process is complete.

Stage 5 Procedure—Alignment of the Candidate:

A depth-first recursive processing of the candidate structure is undertaken, positioning each "current" atom as (or before, see below) it is encountered. This processing begins by simply copying the coordinates of the atoms defining the anchor bond from the template molecule to the candidate molecule, both atoms becoming "positioned".

For each newly encountered "candidate" atom:

Generate a list of the still unencountered atoms attached to this atom, and order these attachments so that no unmatched attachment atom is processed until all matched atoms have been. When this list has been completely processed, backtrack through the recursive tree until an atom having attachments that still needs to be processed is encountered.
  i) If the attached atom has already been positioned (by any of the previous or following alignment operations), proceed immediately and recursively to the processing of its descendant atom, the already positioned atom now becoming the "current" atom.

Otherwise:
  ii) If the bond between this atom and the "current" atom (its parent) is part of a ring while the bond between the atom in the previous atom layer (the parent) and the grandparent atom is non-cyclic, a new candidate ring system (possibly polycyclic, including multiple rings) has been encountered.
    (a) If such a new ring system is also encountered within the template molecule; and the newly encountered ring systems in candidate and template molecules contain the same number of atoms; and there is an exact 2D match between the atomic properties of the matching atoms that form the candidate and template rings; then the 3D coordinates of the template ring atoms are copied to the candidate ring atoms and the candidate ring atoms are thereby "positioned".
    (b) If the conditions in (a) above are not met, the candidate molecule ring atoms, also including all their more distant attachments, are reoriented to a least-squared distance overlay (have the same 3D orientation) with the smallest number of matching template atoms that define a plane. (If there are insufficient matches, all of the candidate ring become "unmatched".) Because the initial 3D structures generated by Concord or Corina may provide different selections among possible ring "puckerings", all possible puckerings of the newly encountered ring atoms are generated, with the puckering that minimizes interatomic distances between candidate and template ring systems being retained. The candidate ring atoms thereby become positioned.
  iii) If the conditions of ii) above are not met, the bond between the atom and its parent atom is acyclic.

If the new candidate atom matches a template atom, the coordinates of the template atom are copied to the candidate atom and the candidate atom becomes positioned.

If the new candidate atom does not match a template atom, all the non-matching attachments to the "current" atom are put onto one list and all their matching template atoms are put onto a second list. Note that each of these attached atoms may be the start of a large branch, so each of these lists is first ordered by the number of heavy atoms that the attachment branch includes, largest to smallest. Then, proceeding in order down both of the lists, the new candidate atom, also including all its more distant attachments, is positioned to exactly overlap its anchor bond (its bond to the "current atom") with the bond between the matching template atoms. If the template list is shorter than the candidate list, then the remaining candidate attachment atoms, including any more distant attached atoms, is positioned using the standard valence rules for the candidate "current atom".

Example 2 noted above establishes the method by which multiple templates are used. The situation contemplates that there are two or more 3D template alignments (possibly from different binding studies). In this case, the method aligns each molecule from each series against each template molecule. One of the alignments which yields the greatest number of positional atom matches is chosen for its CoMFA field generation, the choice being made by criteria described in the auto alignment section below. This alignment is used to generate the CoMFA data table.

Example 3 noted above treats the situation where more than one congeneric series shows activity at the same receptor even though the series are structurally different. Again, all molecules in each series are aligned to the target molecule and the alignment, which finds the greatest number of positional atom matches, is used. The same method is used for Example 4 with multiple congeneric series when more than one template molecule is available. All molecules in each series are aligned to all the target molecules and the alignment which finds the optimal alignment as described in the automatic method below and including greatest number of positional atom matches is used.

Examples 5 and 6 present the case where non-congeneric molecules are found which have activity at the same receptor. They are similarly aligned (as with Examples 3 and 4) to one or more template molecules with the alignment having the greatest number of positional atom matches being used as the final alignment.

Importantly, it should be appreciated that all the candidate molecules that are aligned share the same coordinate space defined by the templates. These molecules are then placed into the three dimensional CoMFA grid for determination of the interaction energies. Those interaction energies when placed into the CoMFA data table provide for the generation of the QSAR. The result is a single QSAR applicable to all the series objectively based on all the data. This result has previously been impossible to achieve and is one of the most significant applications of the present invention.

Automatic Alignment over all Anchor Bonds:

Clearly, a user of the method may examine the effect on alignments of choosing different anchor bonds. Many such alternative selections may be made and the alignments determined.

However, one does not know a priori which anchor bond will produce the best alignment; that is, produce an alignment with the largest number of atom-to-atom matches.

As mentioned above, a distinct advance over the prior art methods of molecular alignment is that it is also possible to comprehensively attempt to align every aspect of each candidate molecule by automating the selection of the anchor bond. At the expense of a great deal of computational time, it is possible to systematically take up every bond in the template structure as an anchor bond and overlay it against every bond in the each molecule to generate alignments. Clearly, however, not all bonds in a template have corresponding bonds in the candidate molecules and much computational time would be taken up generating meaningless alignments. In order to avoid generating meaningless alignment, the following criteria are employed.

1. To reduce the combinatorial number of bond comparisons and the resulting computational time, in both template and candidate structures, every possible anchor bond must meet one of several user-selectable criteria. By default, the initial user-selectable criteria are as follows:
    a. One of the atoms defining the bond must not be carbon, or:
    b. The bond type must be double or triple, or:
    c. One of the atoms defining the bond must be in a ring and attached to at least three non-hydrogen atoms
  2. Additional information is generated for every such bond, of two types. The first positions that bond with respect to any ring network within the overall structure, the ring network being simplified with all its atoms as carbons and all its bonds as single, and including only cyclic bonds, bonds connecting cycling systems, and, if the bond being processed is acyclic, the simplified path connecting the bond to a cyclic system. The second type of information is localized to the bond being processed, and includes the bond type and (a) cyclicality, the types of the defining atoms, the counts of the heavy atoms directly attached to the defining atoms, and the relative proportions of the counts of heavy atoms directly or indirectly attached by the shortest paths to the defining atoms.

3. Selection of the optimal anchor bond match processes all pairings of template bonds meeting one of these criteria with all candidate bonds meeting one of these criteria. The process for selecting the single optimal anchor bond then has two stages.
  a) The first stage generates a list of potential anchor bond pairings by, on the one hand, recognizing the desirable identities between their ring network positionings, and on the other hand, summing undesirable differences between their various localized properties. Only bond pairings whose score exceeds a user-defined threshold become finalist pairings.
  b) In the second stage, the relatively time-consuming connectivity matching procedure described elsewhere in this application is applied to each of the finalist pairings. The finalist pairing that thereby yields the greatest number of matching atoms within any of the templates becomes the anchor bond for that candidate, and the candidate is then aligned by superposition of its anchor bond onto that best-matching bond within any of the templates.

The inventors have found that automatic alignment can routinely be employed with all the example classes described above and provides superior alignments to any accomplished by manual selection of the anchor bonds. The alignment procedure described in this patent document, when implemented with automatic alignment, not only produces meaningful CoMFA analyses but further enables CoMFA to be applied to large assemblages of candidate and template molecules.

Example Application of Use in CoMFA Analysis:

As an exemplary illustration, the method of the present invention was applied to the checkpoint kinase-1 (chk1) therapeutic target as one that has been the subject of extensive work involving a wide range of structures. To perform the required alignments and use them in a CoMFA analysis, the necessary 3D templates were extracted from the first nineteen chk1 protein data base entries referenced at bindingdb.org and the necessary chk1 2D structure activity relationship (SAR) data for 1933 entries was obtained from the ChEMBL compilation of bioactive molecules with drug-like properties. It will be appreciated that this ChEMBL compilation includes hundreds of structural series representing many published attempts to differentiate chemically novel intellectual property. For instance, data from 164 different publications were compiled into the chk1 data.

The 1933 SAR entries were randomly halved into training sets (the odd numbered structures) and test sets (the even numbered structures). The alignment method taught in this patent document was applied to the twelve templates and the 966 training set SAR entries and used to construct a CoMFA data table. The resulting CoMFA analysis produced a satisfactory 7-component CoMFA model. Predictions by this model for the 965 test set are highly useful for drug discovery having a standard deviation of error in prediction of 1.094 log units.

Most importantly, considering the structural diversity of the ChEMBL observations, these predictions were obtained not merely for structures similar to a 3D template, but for any arbitrary structure. Indistinguishable results were obtained by repeating the calculation after exchange of training and test sets Methods available in the prior art could not attempt to align such a diversity and quantity of structures. However, many chk1-tested structures contain an amide bond, so to provide an objective standard for comparison, the same training set molecules were instead aligned by overlay of the amide bonds of their Concord models. Because of missing or ambiguously multiple occurrences of amide bonds, only 230 of the structures were thus usable. It may be noted therefore that the structural scope of any model that might have resulted would have been limited. In fact, in the derived CoMFA analysis from an overlay of amide bonds, the cross-validated $r^2$ for the resulting model was 0.00 indicating its uselessness for prediction.

I claim:

1. A computer implemented drug discovery method utilizing a specifically programmed computer for aligning in three dimensions a candidate molecule exhibiting a common activity to a specified template molecule comprising the following steps:
   specifying a candidate molecule that is to be aligned to a template molecule;
   generating a 3D structure for the candidate molecule determining valances, bond angles, and bond lengths;
   specifying a template molecule with an identified 3D structure;
   specifying an anchor bond in the candidate molecule;
   specifying an anchor bond in the template molecule;
   orienting the candidate molecule by superimposing its anchor bond onto the template anchor bond;
   enumerating for both template and candidate molecule all atoms and atom properties excluding all hydrogen atoms;
   matching similar atoms or atom properties in the template and candidate molecule by sequential traversals of the molecules that start at the anchor bond and ending wherever no more property matches exist along any connected path;
   assigning the coordinates of template atoms to the matching candidate atoms;
   positioning any atoms in the candidate molecule that do not have matching atoms in the template molecule by assigning coordinates to those atoms so as to maintain their relative positions to those atoms in the candidate molecule that had matching atoms in the template molecule;
   aligning and assigning coordinates to atoms in any branch that includes only uncoordinated-copied atoms using the topomer alignment rules or any similar systematic procedure to consistently place the atoms in the branch; and
   outputting the coordinates for the candidate molecule alignment.

2. The method of claim 1, in which a CoMFA analysis is performed based upon a data table consisting of molecular shape descriptors generated using the resulting molecular alignment along with the activity data associated with each aligned molecule.

3. A computer implemented drug discovery method utilizing a specifically programmed computer for aligning in three dimensions candidate molecules exhibiting a common activity to a specified set of template molecules comprising the following steps:
   a) specifying a candidate molecule that is to be aligned to a template molecule;
   b) generating a 3D structure for the candidate molecule determining valances, bond angles, and bond lengths;
   c) specifying a template molecule with an identified 3D structure;
   d) specifying an anchor bond in the candidate molecule;
   e) specifying an anchor bond in the template molecule;
   f) orienting the candidate molecule by superimposing its anchor bond onto the template anchor bond;

g) enumerating for both template and candidate molecule all atoms and atom properties excluding all hydrogen atoms;

h) matching similar atoms or atom properties in the template and candidate molecule by sequential traversals of the molecules that start at the anchor bond and ending wherever no more property matches exist along any connected path;

i) assigning the coordinates of template atoms to the matching candidate atoms identified in step h;

j) positioning any atoms in the candidate molecule that do not have matching atoms in the template molecule by assigning coordinates to those atoms so as to maintain their relative positions to those atoms in the candidate molecule that had matching atoms in the template molecule;

k) aligning and assigning coordinates to atoms in any branch that includes only uncoordinated-copied atoms using the topomer alignment rules or any similar systematic procedure to consistently place the atoms in the branch;

l) retaining the alignment if it is better than any proceeding alignment;

m) repeating steps e) through I) for all bonds in the template molecule;

n) repeating steps d) through m) for all bonds in the candidate molecule;

o) repeating steps c) through n) for all template molecules;

p) repeating steps a) through o) for all candidate molecules; and q) outputting the coordinates for each candidate alignment.

4. The method of claim 3 in which a CoMFA analysis is performed based upon a data table consisting of molecular shape descriptors generated using the resulting molecular alignments along with the activity data associated with each aligned molecule.

* * * * *